US00PP23727P2

(12) United States Plant Patent
Kraan

(10) Patent No.: US PP23,727 P2
(45) Date of Patent: Jul. 9, 2013

(54) ***HYDRANGEA* PLANT NAMED 'SAVILL LACE'**

(50) Latin Name: *Hydrangea paniculata*
Varietal Denomination: Savill Lace

(75) Inventor: Kees Jan Kraan, Papenveer (NL)

(73) Assignee: Boot & Co Boomkwekerijen BV, Boskoop (NL)

( * ) Notice: Subject to any disclaimer, the term of this patent is extended or adjusted under 35 U.S.C. 154(b) by 81 days.

(21) Appl. No.: 13/317,617

(22) Filed: Oct. 24, 2011

(51) Int. Cl.
*A01H 5/00* (2006.01)

(52) U.S. Cl.
USPC ..... Plt./250

(58) Field of Classification Search
USPC ..... Plt./250
See application file for complete search history.

*Primary Examiner* — Annette Para
(74) *Attorney, Agent, or Firm* — Mark P. Bourgeois

(57) ABSTRACT

A new cultivar of *Hydrangea* plant named 'Savill Lace' that is characterized by a semi-compact broad habit, large conical flower panicles with fertile and sterile flowers, sterile flower sepals that are green-white when young, mature to white and fade to purplish and purple-red tinged fertile flower buds that open to white flowers.

1 Drawing Sheet

Botanical classification: *Hydrangea paniculata.*
Variety denomination: 'Savill Lace'.

BACKGROUND OF THE INVENTION

The present invention relates to a new and distinct cultivar of *Hydrangea* plant botanically known as *Hydrangea paniculata* and hereinafter referred to by the cultivar name 'Savill Lace'.

The new cultivar is the product of a breeding program conducted by the inventor in a cultivated area of Boskoop, The Netherlands. The objective of the breeding program was to develop new *Hydrangea* cultivars with a compact habit and attractive flowers.

'Savill Lace' originated from open pollination of the female or seed parent an unnamed proprietary cultivar of *Hydrangea paniculata* (not patented) in 2003. The male or pollen parent is unknown. The cultivar 'Savill Lace' was selected by the inventor in 2007 as a single plant in Boskoop, The Netherlands.

Asexual reproduction by cuttings of the new cultivar 'Savill Lace' was first performed in 2007 in Boskoop, The Netherlands. Since that time, under careful observation, the unique characteristics of the new *Hydrangea* cultivar have been uniform, stable and reproduced true to type in successive generations of asexual reproduction.

SUMMARY OF THE INVENTION

The following represent the distinguishing characteristics of the new *Hydrangea* cultivar 'Savill Lace'. These traits in combination distinguish 'Savill Lace' as a new and distinct cultivar apart from all other existing varieties of *Hydrangea* known to the inventor. 'Savill Lace' has not been tested under all possible conditions and phenotypic differences may be observed with variations in environmental, climatic, and cultural conditions, however, without any variance in genotype.

1. *Hydrangea* 'Savill Lace' exhibits a semi-compact broad habit.

2. *Hydrangea* 'Savill Lace' exhibits large conical flower panicles with fertile and sterile flowers.
3. *Hydrangea* 'Savill Lace' exhibits sterile flower sepals that are green-white when young, mature to white and fade to purplish.
4. *Hydrangea* 'Savill Lace' exhibits purple-red tinged fertile flower buds that open to white flowers.

The closest comparison plants are *Hydrangea* 'Kyushu' (not patented) and *Hydrangea* 'Greenspire' (not patented)

'Savill Lace' is distinguishable from 'Kyushu' in having longer and wider flower panicles and sterile flowers that are more green when opening and that fade to purplish. The sterile flowers of 'Kyushu' do not fade. 'Savill Lace' has flower buds that are tinged purple-red. The flower buds of 'Kyushu' are cream colored.

'Savill Lace' is distinguishable from 'Greenspire' in having longer and wider flower panicles and sterile flowers that mature to white and then fade to purplish. The sterile flowers of 'Greenspire' are cream white when mature and do not fade. 'Savill Lace' has a broad semi-compact habit. 'Greenspire' has a taller and narrower habit.

The new cultivar 'Savill Lace' is distinguishable from the unnamed female parent in having a broad semi-compact habit. The unnamed female parent plant has a taller more upright habit. 'Savill Lace' has larger flower panicles than the unnamed female parent plant. 'Savill Lace' has sterile flowers that open green-white. The sterile flowers of the unnamed female parent plant open cream-white.

BRIEF DESCRIPTION OF THE DRAWING

The accompanying photograph illustrates the distinguishing traits of *Hydrangea* 'Savill Lace'. The plant in the photograph shows an overall view of a four year old outdoor field grown plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Hydrangea* cultivar named 'Savill Lace'. Data was collected in Boskoop, The Netherlands from four year old outdoor field grown plants. The time of year was September and the temperatures ranged from 14-28° Centigrade during the day, and 6-15° Centigrade during the night. The light level was natural outdoor light and there were no photoperiodic treatments or growth retardants used. Color determinations are in accordance with The Royal Horticultural Society Colour Chart, 5$^{th}$ edition 2007, except where general color terms of ordinary dictionary significance are used. The growing requirements are similar to the species.

Botanical classification: *Hydrangea paniculata* 'Savill Lace'.

Parentage: 'Savill Lace' resulted from open pollination between the female parent an unnamed proprietary cultivar of *Hydrangea paniculata* and an unknown male parent.

Vigor: Moderate.

Growth rate: Moderate.

Growth habit: Broad upright.

Plant shape: Globe shaped.

Suitable container size: 2 liter.

Height: Average 125 cm. in height.

Width: Average 150 cm. in diameter.

Low temperature tolerance: USDA Zone 5.

High temperature tolerance: USDA Zone 9.

Propagation: Softwood cuttings.

Time to initiate roots: Approximately 26 weeks are required to produce a rooted plant.

Crop time: Approximately 12 months are required to achieve a finished plant from a rooted cutting.

Root system: Fine and fibrous.

Stem:

*Branching habit*.—Free branching.
*Basal branching*.—Yes.
*Average number of lateral branches*.—56.
*Pinching*.—No.
*Lateral branch diameter*.—Average 6 mm. in diameter.
*Lateral branch length*.—Average 67.9 cm. in length.
*Stem angle*.—Average 45 degrees from soil plane.
*Stem strength*.—Strong.
*Stem color immature*.—146D to 199A, sunny side 178A.
*Stem color mature*.—199B to N199B.
*Pubescence*.—Absent.
*Internode length*.—Approximately 4.8 cm. between nodes.
*Shape*.—Rounded, smooth.

Foliage:

*Leaf arrangement*.—Opposite or in whorls of three.
*Leaf shape*.—Ovate.
*Leaf tip*.—Short apiculate.
*Leaf base*.—Rounded.
*Leaf margin*.—Serrate.
*Leaf dimensions*.—Length: 12.2 cm, width: 6.4 cm.
*Texture upper side*.—Dull, slightly rugose.
*Texture under side*.—Dull, slightly rugose.
*Pubescence*.—Upper side sparsely covered with short adpressed hairs, 0.75 mm. in length, color NN155C to NN155D. Main and secondary veins and vein-axils on lower side covered with short hairs, 0.75 mm. in length, color 156D.
*Vein pattern*.—Pinnate.
*Leaf color young, upper surface*.—137B to 143A.
*Leaf color young, lower surface*.—138A.
*Leaf color mature, upper surface*.—N137A.
*Leaf color mature, lower surface*.—147B.
*Vein color, upper side*.—146D.
*Vein color, under side*.—147D.
*Leaf attachment*.—Petiolate.
*Petiole dimensions*.—2.0 cm. in length and 3.0 mm. in diameter.
*Petiole texture upper side*.—Dull, moderately pubescent with hairs 0.5 mm. in length, color 156D.
*Petiole texture under side*.—Dull, sparsely pubescent with hairs 0.5 mm. in length, color 156D.
*Petiole color upper side*.—183B.
*Petiole color under side*.—Varies between 147D and 156A.

Flower:

*Flowering season*.—Summer to early autumn.
*Time to flower from planting*.—Approximately 1 year.
*Fragrance*.—None.
*Inflorescence type*.—Broad conical lacecap panicles.
*Panicle height*.—Average 23.4 cm. in height.
*Panicle diameter*.—Average 19.2 cm. in diameter.

Sterile flowers:

*Bud length*.—Average 5.0 mm. in length.
*Bud diameter*.—Average 4 mm. in diameter.
*Bud shape*.—Flattened globose.
*Bud color*.—145B.
*Quantity of sterile flowers per inflorescence*.—Average 100.
*Aspect*.—Upright to slightly outward, drooping when fading.
*Shape*.—Rotate.
*Dimensions*.—Average 5.3 cm. in diameter and 1.2 cm. in height.
*Longevity*.—Approximately 2 to 3 weeks.
*Persistent or self-cleaning*.—Persistent.
*Number of petals*.—Four in number.
*Petal arrangement*.—Rotate.
*Petal shape*.—Ovate.
*Petal margin*.—Entire.
*Petal apex*.—Acute.
*Petal base*.—Cuneate.
*Petal dimensions*.—Average 3.0 mm. in length and 1.5 mm. in width.
*Petal texture*.—Smooth and slightly glossy both sides.
*Petal color when opening* (*upper side*).—NN155D.
*Petal color when opening* (*under side*).—NN155D.
*Petal color fully opened* (*upper side*).—155A.
*Petal color fully opened* (*under side*).—NN155A.
*Petal color fading to*.—Not fading.
*Number of sepals*.—50% of sterile flowers has 4 sepals and 50% have 5 sepals.
*Sepal arrangement*.—Rotate.
*Sepal shape*.—Broad obovate to broad ovate.
*Sepal margin*.—Entire.
*Sepal apex*.—Obtuse.
*Sepal base*.—Cuneate.
*Sepal dimensions*.—Average 2.5 cm. in length and 2.1 cm. in width.
*Sepal surface*.—Smooth, dull both surfaces.
*Sepal color, young* (*upper side*).—150C.
*Sepal color, young* (*under side*).—145C.
*Sepal color, mature* (*upper side*).—150D to 155A, slightly flushed 145B.
*Sepal color, mature* (*under side*).—150D to 155A.
*Sepal color fading to* (*upper side*).—144B to 144C, slightly flushed 182D.
*Sepal color fading to* (*under side*).—184C, slightly flushed 177D.

*Pedicel dimensions*.—Average 2.5 cm. in length and 1.0 mm. in diameter.
*Pedicel angle*.—50° from vertical.
*Pedicel strength*.—Moderate.
*Pedicel texture*.—Dull with short adpressed hairs, 1 mm in length, NN155D in color.
*Pedicel color*.—150D.
*Androecium*.—Yes.
*Stamen number*.—Average 8.
*Filament length*.—Average 2.5 mm.
*Filament color*.—NN155C.
*Anther shape*.—Double kidney shaped.
*Anther length*.—0.5 mm.
*Anther color*.—186D.
*Amount of pollen*.—Low.
*Pollen color*.—156A.
*Gynoecium*.—Yes.
*Number of pistils*.—Average 3.
*Pistil length*.—1.5 mm.
*Stigma shape*.—Club shaped.
*Stigma color*.—157A.
*Style length*.—1.0 mm.
*Style color*.—157D.
*Ovary color*.—143A.

Fertile flowers:
*Bud length*.—Average 4.0 mm. in length.
*Bud diameter*.—Average 3 mm. in diameter.
*Bud shape*.—Flattened globose.
*Bud color*.—145A to 145B, tip 157D tinged 62C to 62D.
*Quantity of fertile flowers per inflorescence*.—Average 650.
*Aspect*.—Upright to outward.
*Shape*.—Rotate.
*Dimensions*.—Average 7.0 mm. in diameter and 5.0 mm. in height.
*Longevity*.—Approximately 1 week.
*Persistent or self-cleaning*.—Self-cleaning.
*Number of petals*.—Five in number.
*Petal arrangement*.—Rotate.
*Petal shape*.—Ovate.
*Petal margin*.—Entire.
*Petal apex*.—Acute.
*Petal base*.—Cuneate.
*Petal dimensions*.—Average 3.0 mm. in length and 1.5 mm. in width.
*Petal texture*.—Smooth and slightly glossy both sides.
*Petal color when opening* (*upper side*).—NN155D.
*Petal color when opening* (*under side*).—NN155D.
*Petal color fully opened* (*upper side*).—155A.
*Petal color fully opened* (*under side*).—NN155A.
*Petal color fading to*.—Not fading.
*Number of sepals*.—Average 5.
*Sepal arrangement*.—Rotate.
*Sepal shape*.—Triangular.
*Sepal margin*.—Entire.
*Sepal apex*.—Broad acute.
*Sepal base*.—Broad cuneate.
*Sepal dimensions*.—Average 1.0 mm. in length and 1.0 mm. in width.
*Sepal surface*.—Smooth, slightly glossy both surfaces.
*Sepal color, young* (*upper side*).—150D.
*Sepal color, young* (*under side*).—150D.
*Sepal color, mature* (*upper side*).—150D.
*Sepal color, mature* (*under side*).—150D.
*Sepal color fading to* (*upper side*).—Not fading.
*Sepal color fading to* (*under side*).—Not fading.
*Pedicel dimensions*.—Average 3.0 mm. in length and 0.5 mm. in diameter.
*Pedicel strength*.—Moderate.
*Pedicel texture*.—Smooth, dull.
*Pedicel angle*.—Varies in all angles.
*Pedicel color*.—150D.
*Stamen number*.—Average 10.
*Filament length*.—Average 3.5 mm.
*Filament color*.—NN155D.
*Anther shape*.—Double kidney shaped.
*Anther length*.—0.5 mm.
*Anther color*.—186D.
*Amount of pollen*.—Low.
*Pollen color*.—156A.
*Number of pistils*.—3.
*Pistil length*.—2 mm.
*Stigma shape*.—Flattened on top of style.
*Stigma color*.—157D.
*Style length*.—1.0 mm.
*Style color*.—145D.
*Ovary color*.—145A.

Seed: Seed development has not been observed to date.
Disease and pest resistance: Has not been observed to date.

It is claimed:

1. A new and distinct variety of *Hydrangea* plant named 'Savill Lace' as described and illustrated.

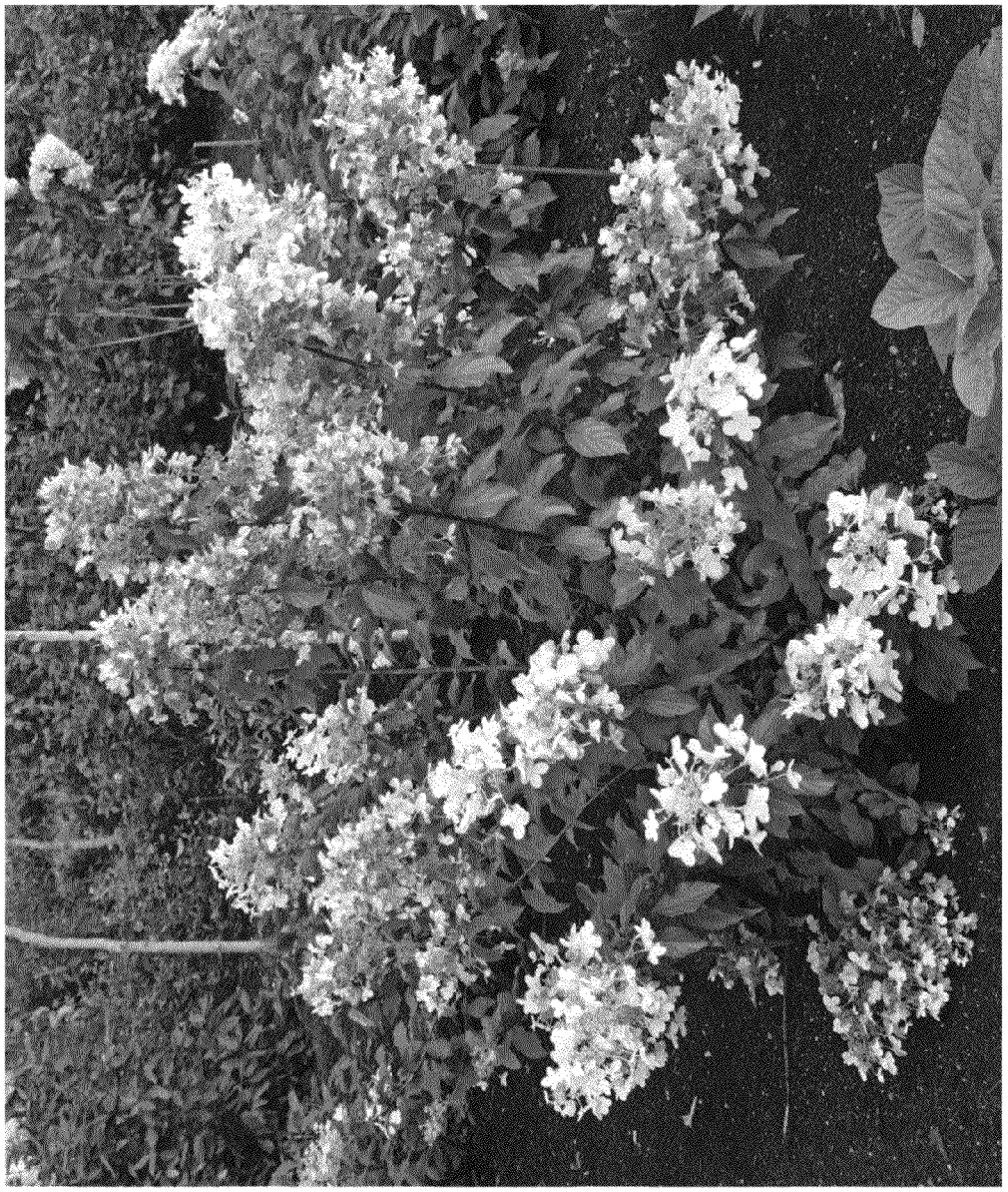

* * * * *